(12) United States Patent
Cho et al.

(10) Patent No.: US 8,637,667 B2
(45) Date of Patent: Jan. 28, 2014

(54) METHOD FOR PREPARING (S)-5-CHLORO-N-((3-(4-(5,6-DIHYDRO-4H-1,2,4-OXADIAZIN-3-YL)PHENYL)-2-OXOOXAZOLIDIN-5-YL)METHYL)THIOPHENE-2-CARBOXAMIDE DERIVATIVES

(75) Inventors: Young Lag Cho, Daejeon (KR); Jong Un Cho, Daejeon (KR); Sung Yoon Baek, Daejeon (KR); Ho Young Song, Daejeon (KR); Tae Kyo Park, Daejeon (KR); Sung Ho Woo, Daejeon (KR); Yong Zu Kim, Daejeon (KR)

(73) Assignee: Legochem Bioscience Ltd., Daejeon (KR)

( * ) Notice: Subject to any disclaimer, the term of this patent is extended or adjusted under 35 U.S.C. 154(b) by 200 days.

(21) Appl. No.: 13/382,265

(22) PCT Filed: Jul. 7, 2010

(86) PCT No.: PCT/KR2010/004420
§ 371 (c)(1),
(2), (4) Date: Jan. 4, 2012

(87) PCT Pub. No.: WO2011/005028
PCT Pub. Date: Jan. 13, 2011

(65) Prior Publication Data
US 2012/0108808 A1     May 3, 2012

(30) Foreign Application Priority Data

Jul. 8, 2009 (KR) .................... 10-2009-0062122

(51) Int. Cl.
| C07D 413/02 | (2006.01) |
| C07D 413/04 | (2006.01) |
| C07D 273/04 | (2006.01) |

(52) U.S. Cl.
USPC .......................................... 544/66; 514/229.2

(58) Field of Classification Search
USPC .......................................................... 544/66
See application file for complete search history.

(56) References Cited

U.S. PATENT DOCUMENTS

2003/0153610 A1    8/2003   Straub et al.

FOREIGN PATENT DOCUMENTS

| KR | 10-0898361 B1 | 5/2009 |
| WO | WO 01/47919 A1 | 7/2001 |

*Primary Examiner* — Kahsay Habte
(74) *Attorney, Agent, or Firm* — Sughrue Mion, PLLC

(57) ABSTRACT

Provided is a method for preparing (S)-5-chloro-N-((3-(4-(5,6-dihydro-4H-1,2,4-oxadiazin-3-yl)phenyl)-2-oxooxazolidin-5-yl)methyl)thiophene-2-carboxamide derivatives of Formula (I) which are useful as blood coagulation factor Xa inhibitors, and said method using 1-fluoro-4-nitrobenzen as a starting material. According to the method of the present invention, (S)-5-chloro-N-((3-(4-(5,6-dihydro-4H-1,2,4-oxadiazin-3-yl)phenyl)-2-oxooxazolidin-5-yl)methyl) thiophene-2-carboxamide derivatives of Formula (I) which are useful as blood coagulation factor Xa inhibitors can be prepared in a high purity and a high yield.

3 Claims, No Drawings

METHOD FOR PREPARING (S)-5-CHLORO-N-((3-(4-(5,6-DIHYDRO-4H-1,2,4-OXADIAZIN-3-YL)PHENYL)-2-OXOOXAZOLIDIN-5-YL)METHYL)THIOPHENE-2-CARBOXAMIDE DERIVATIVES

CROSS REFERENCE TO RELATED APPLICATIONS

This application is a National Stage of International Application No. PCT/KR2010/004420 filed Jul. 7, 2010, claiming priority based on Korean Patent Application No. 10-2009-0062122 filed Jul. 8, 2009 the contents of all of which are incorporated herein by reference in their entirety.

FIELD OF THE INVENTION

The present invention relates to a method for preparing (S)-5-chloro-N-((3-(4-(5,6-dihydro-4H-1,2,4-oxadiazin-3-yl)phenyl)-2-oxooxazolidin-5-yl)methyl)thiophene-2-carboxamide derivatives of Formula (I) which are useful as blood coagulation factor Xa inhibitors.

(I)

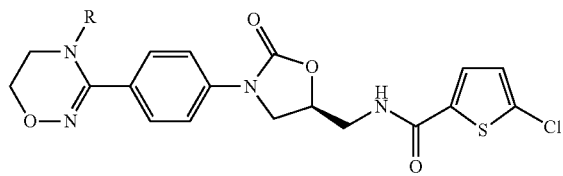

BACKGROUND OF THE INVENTION (S)-5-chloro-N-((3-(4-(5,6-dihydro-4H-1,2,4-oxadiazin-3-yl)phenyl)-2-oxooxazolidin-5-yl)methyl)thiophene-2-carboxamide of Formula (I-A) serves as an inhibitor against blood coagulation factor Xa and can be used for treating and preventing thrombosis, myocardial infarction, arteriosclerosis, inflammatory, apoplexy, angina pectoris, recurrent stricture after angioplasty, and thromboembolism such as intermittent claudication.

(I-A)

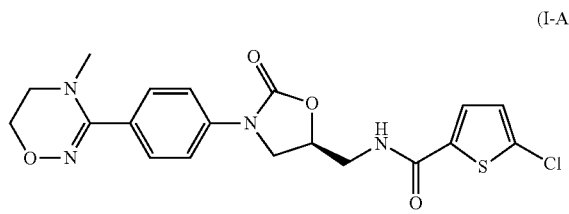

The method for preparing the above-mentioned compound having an inhibitory effect against factor Xa is disclosed in Korean Patent No. 898361 which is filed by the present inventors. However, said method has problems in that the total production yield is low and column chromatography must be employed in the purification process of each step, which makes it not suitable for mass production.

SUMMARY OF THE INVENTION

Therefore, it is an object of the present invention to provide a novel and simple method for preparing a high purity (S)-5-chloro-N-((3-(4-(5,6-dihydro-4H-1,2,4-oxadiazin-3-yl)phenyl)-2-oxooxazolidin-5-yl)methyl)thiophene-2-carboxamide derivatives in a high total yield by using a crystallization or extraction process suitable for industrial-scale isolation and purification processes.

Further, it is an object of the present invention to provide an intermediate used for preparing (S)-5-chloro-N-((3-(4-(5,6-dihydro-4H-1,2,4-oxadiazin-3-yl)phenyl)-2-oxooxazolidin-5-yl)methyl)thiophene-2-carboxamide derivatives and a preparation method thereof.

DETAILED DESCRIPTION OF THE INVENTION

Hereinafter, the present invention is described in detail.

The present invention provides a method for preparing an (S)-5-chloro-N-((3-(4-(5,6-dihydro-4H-1,2,4-oxadiazin-3-yl)phenyl)-2-oxooxazolidin-5-yl)methyl)thiophene-2-carboxamide derivative of Formula (I) which is useful as a blood coagulation factor Xa inhibitor, and an intermediate thereof.

Further, the compound of Formula (I) may be in the form of one of various salts thereof. The method is applicable to industrial-scale production and, in particular, the present invention includes a novel synthetic method for preparing a cyclic amidoxime group in the method for preparing the compound of Formula (I). In addition, for the chemical synthesis suitable for industrial-scale production, the present invention includes a method for preparing an intermediate or an addition salt thereof which is useful in a cost-effective crystallization process.

(I)

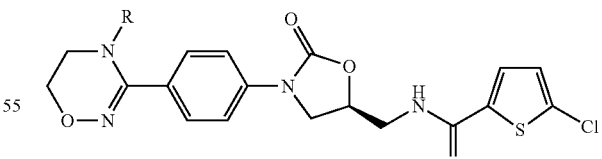

wherein,

R is hydrogen, $C_1$-$C_7$ alkyl, $C_3$-$C_7$ cycloalkyl, or $C_6$-$C_{12}$ aryl.

The process for preparing the compound of Formula (I) is depicted in Reaction Scheme (II).

<Reaction Scheme II>

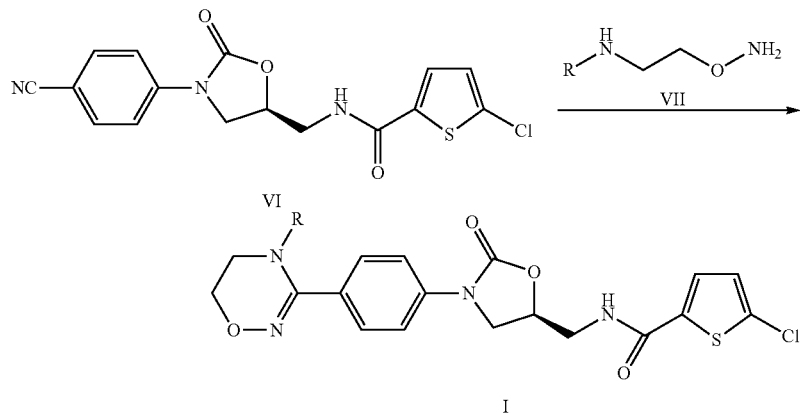

Referring to Reaction Scheme (II), the cyano group of the oxazolidinone compound of Formula (VI) is converted into an imidate by treating with bubbling gaseous HCl in an alcoholic solvent, and the resulting imidate is subjected to a cyclization reaction with a diamine compound of Formula (VII), to obtain a cyclic amidoxime compound of Formula (I). The alcoholic solvent used herein may be methanol or ethanol, preferably anhydrous methanol. The bubbling of gaseous HCl is preferably carried out at 0° C. and slowly increasing the temperature to room temperature. Further, the reaction with the diamine compound may be carried out in an alcohol such as methanol or ethanol, or a conventional organic solvent, preferably acetic acid. The cyclic amidoxime compound thus obtained, may be purified by acid-base extraction, and may be further recrystallized from an organic solvent so as to increase its purity. The solvent is preferably an alcohol such as methanol or ethanol.

The oxazolidinone compound of Formula (VI), a starting material for preparing the cyclic amidoxime compound, is prepared by either of the procedure of Reaction Schemes (III) and (VI).

<Reaction Scheme III>

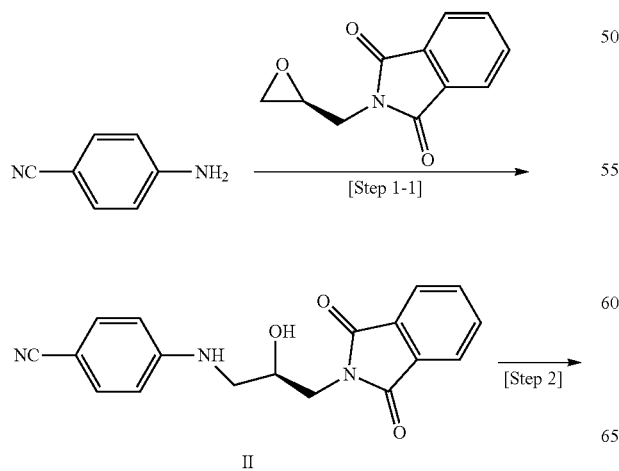

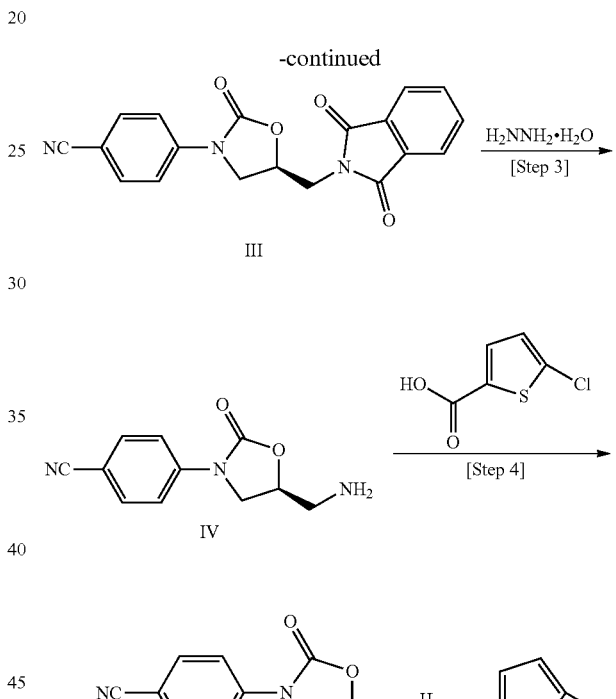

<Reaction Scheme VI>

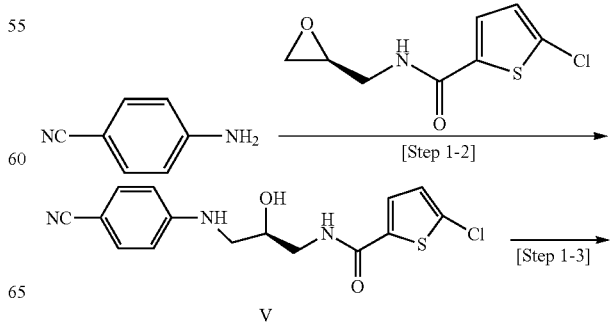

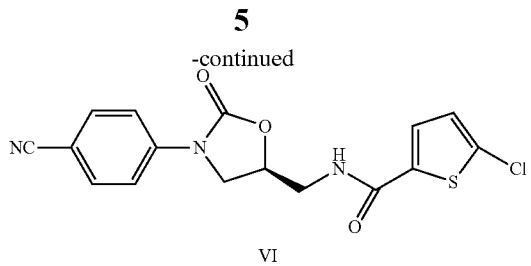

VI

Hereinafter, each step is described in detail.

[Step 1-1] Preparation of the Compound of Formula (II)

In order to prepare the compound of Formula (II), 4-aminobenzonitrile and (S)-glycidyl phthalimide are subjected to a condensation reaction. In this reaction, no solvent is used. Typically, the reaction may be carried out at a wide range of temperature, e.g., about 80° C. to 120° C., preferably 90° C. to 140° C., and more preferably 95° C. to 115° C.

In an embodiment of the present invention, the reaction may be carried out by heating in the presence of about 1 molar equivalent of (S)-glycidyl phthalimide at a temperature of 105° C., preferably for 10 to 15 hours, followed by recrystallization using a mixed solvent of isopropanol and methylene chloride to obtain the compound of Formula (II).

[Step 1-2] Preparation of the Compound of Formula (V)

The compound of Formula (V) is obtained by a nucleophilic substitution reaction of 4-aminobenzonitrile with 5-chloro-N-(((S)-oxiran-2-yl)methyl)thiopene-2-carboxamide. 5-chloro-N-(((S)-oxiran-2-yl)methyl)thiopene-2-carboxamide can be purchased from RStech Corporation in Korea. 5-chloro-N-(((S)-oxiran-2-yl)methyl)thiopene-2-carboxamide is preferably used in an excess amount of 1 to 2 molar ratio, but may be also used in a stochimetric amount. The examples of the solvent used herein include, but not limited thereto, alcohols such as isopropanol or isobutanol; nitriles such as acetonitrile; esters such as ethyl acetate; chlorinated hydrocarbons such as dichloromethane or 1,2-dichloromethane; ethers such as tetrahydrofuran, diisopropylether, dioxane or 1,2-dimethoxyethane; aromatic hydrocarbons such as benzene or toluene, and amides such as dimethylacetamide or dimethylformamide. Such solvent may be used as a single or a mixed solvent. The reaction is performed at a temperature ranging from a boiling point of solvent to 20~80° C.

[Step 1-3] Preparation of the Compound of Formula (VI)

The oxazolidinone compound of Formula (VI) is obtained by subjecting a vicinal amino alcohol compound of Formula (V) to a carbonylation reaction with a phosgene equivalent such as ethyl chloroformate or 1,1'-carbonyldiimidazole, as a condensing agent. In the present invention, 1,1'-carbonyldiimidazole is preferably used as a phosgene equivalent, and di($C_1$-$C_4$)alkylaminopyridines or N-heterocycloalkylpyridines, e.g., 4-dimethylaminopyridine or 4-pyrrolidinopyridine is used as an activating agent. Generally, the phosgene equivalent condensing agent is used in an excess amount of 1 to 3 molar ratio based on the compound of Formula (V), and the activating agent is used in a stochimetric amount or less based on the compound of Formula (V). Typically, the reaction may be carried out at a wide range of temperature, for example, about 20° C. to 150° C., preferably at a temperature having a solvent refluxed, i.e., 40° C. to 100° C., and more preferably at a temperature of 60° C. to 90° C. The examples of the solvent used herein include, nitriles such as acetonitrile; esters such as ethyl acetate; chlorinated hydrocarbons such as dichloromethane or 1,2-dichloromethane; ethers such as tetrahydrofuran, diisopropylether, dioxane or 1,2-dimethoxyethane; aromatic hydrocarbons such as benzene or toluene; amides such dimethylacetamide or dimethylformamide; and a mixture thereof.

[Step 2] Preparation of the Compound of Formula (III)

The oxazolidinone compound of Formula (III) is obtained by subjecting a vicinal amino alcohol Compound of Formula (II) to a carbonylation reaction with a phosgene equivalent such as ethyl chloroformate or 1,1'-carbonyldiimidazole, as a condensing agent. In the present invention, 1,1'-carbonyldiimidazole is preferably used as a phosgene equivalent, and di($C_1$-$C_4$)alkylaminopyridines or N-heterocycloalkylpyridines, e.g., 4-dimethylaminopyridine or 4-pyrrolidinopyridine is used as an activating agent. Generally, the phosgene equivalent condensing agent is used in an excess amount of 1 to 3 molar ratio based on the compound of Formula (II), and the activating agent is used in a stochimetric amount or less based on the compound of Formula (II). Typically, the reaction may be carried out at a wide range of temperature, for example, about 20° C. to 150° C., preferably at a temperature having a solvent refluxed, i.e., 40° C. to 100° C., and more preferably at a temperature of 60° C. to 90° C. The examples of the solvent used herein include, nitriles such as acetonitrile; esters such as ethyl acetate; chlorinated hydrocarbons such as dichloromethane or 1,2-dichloromethane; ethers such as tetrahydrofuran, diisopropylether, dioxane or 1,2-dimethoxyethane; aromatic hydrocarbons such as benzene or toluene; amides such dimethylacetamide or dimethylformamide; and a mixture thereof.

In an embodiment of the present invention, the compound of Formula (II) is treated with 1~1.5 equivalent of 1,1'-carbonyldiimidazole in the presence of 0.1~0.3 equivalent of 4-dimethylaminopyridine and a solvent, preferably dimethylformamide, and this reaction is carried out by stirring the resulting mixture while refluxing at 60° C. to 100° C., appropriately at 80° C. for 5 to 20 hours, and more appropriately for 10 to 15 hours. In the work-up procedure, the reaction mixture is concentrated under a reduced pressure, and the residue is recrystallized with isopropanol, followed by a simple filtration process, to obtain the oxazolidinone compound of Formula (III).

[Step 3] Preparation of the Primary Amine Compound of Formula (IV)

The primary amine compound of Formula (IV) is obtained by treating the oxazolidinone compound of Formula (III) with hydrazine, to deprotect (or remove) phthalimide, i.e., a protective group for N atom. Examples of the solvent used herein include, but not limited thereto, alcohols such methanol or ethanol, chlorinated hydrocarbons such as dichloromethane or 1,2-dichloromethane; ethers such as tetrahydrofuran, diisopropylether, dioxane or 1,2-dimethoxyethane; aromatic hydrocarbons such as benzene or toluene; amides such dimethylacetamide or dimethylformamide; and a mixture thereof. The deprotection reaction of said amine protective group is well known in the art of organic synthesis, and for example, is described in L. Paquette, ed. Encyclopedia of Reagents for Organic Synthesis, John Wiley and Sons (1995); and T. W Greene and P. G. W Wuts, Protective Group in Organic Synthesis, $2^{nd}$ ed., John Wikey and Sons, New York, Chapter 7, 1991.

The reaction is preferably carried out by treating the compound of Formula (III) with 1~4 equivalent of hydrazine in a mixed solvent of methanol and methylene chloride. Appropriately, the resulting mixture is stirred at a refluxing temperature for 5 hours. In the work-up procedure, a fractional recrystallization is used so as to remove phthalhydrazide, which is formed as a white solid by cooling the reaction mixture, by filtration. The filtrate is then concentrated, and the residue is recyallized with isopropanol, followed by a simple filtration, to obtain the primary amine compound of Formula (IV).

[Step 4] Preparation of the Compound of Formula (VI)

The compound of Formula (VI) is obtained by subjecting the primary amine compound of Formula (IV) to a condensation reaction with 5-chlorothiopene-2-carboxylic acid. This condensation reaction may be carried out by various methods known in the art of organic synthesis. In the present invention, dimethylformamide is preferably used as a solvent and 4-hydroxybenzotriazole and 1-[3-(dimethylamino)propyl]-3-ethylcarbodiimide are used as activating agents. In the work-up procedure, the reaction mixture is cooled, a nonpolar solvent, suitably cyclohexane, and distilled water are added thereto while stirring the mixture, and the precipitated compound of Formula (VI) is isolated by filtration.

In one embodiment of the present invention, the cyclic amidoxime compound of Formula (I) is prepared as follows:

1-1) conducting a condensation reaction of 4-aminobenzonitrile with (S)-glycidyl phthalimide, to obtain the compound of Formula (II);
2) carbonylating the compound of Formula (II) with ethyl chloroformate or 1,1'-carbonyldiimidazole to obtain the oxazolidinone ring compound of Formula (III);
3) treating the oxazolidinone compound of Formula (III) with hydrazine so as to remove the phthalimide nitrogen atom protective group, to obtain the primary amine compound of Formula (IV);
4) treating the primary amine compound of Formula (IV) with 5-chlorothiopene-2-carboxylic acid, to obtain the compound of Formula (VI) having introduced 5-chlorothiopene-2-carbonyl group; and
5) treating the cyano group of the oxazolidinone compound of Formula (VI) with HCl in an alcoholic solvent and subjecting to a cyclization reaction with the diamine compound of Formula (VII), to obtain the cyclic amidoxime compound of Formula (I).

In another embodiment of the present invention, the cyclic amidoxime compound of Formula (I) is prepared as follow:

1-2) treating 4-aminobenzonitrile with 5-chloro-N-((S)-oxiran-2-yl)methyl)thiopene-2-carboxamide to obtain the compound of Formula (V);
1-3) carbonylating the compound of Formula (V) with ethyl chloroformate or 1,1'-carbonyldiimidazole to obtain the oxazolidinone ring compound of Formula (VI); and
5) treating the cyano group of the oxazolidinone compound of Formula (VI) with HCl in an alcoholic solvent and subjecting to a cyclization reaction with the diamine compound of Formula (VII), to obtain the cyclic amidoxime compound of Formula (I).

The total procedure for preparing the cyclic amidoxime of the Formula (I) is depicted in Reaction Scheme (V).

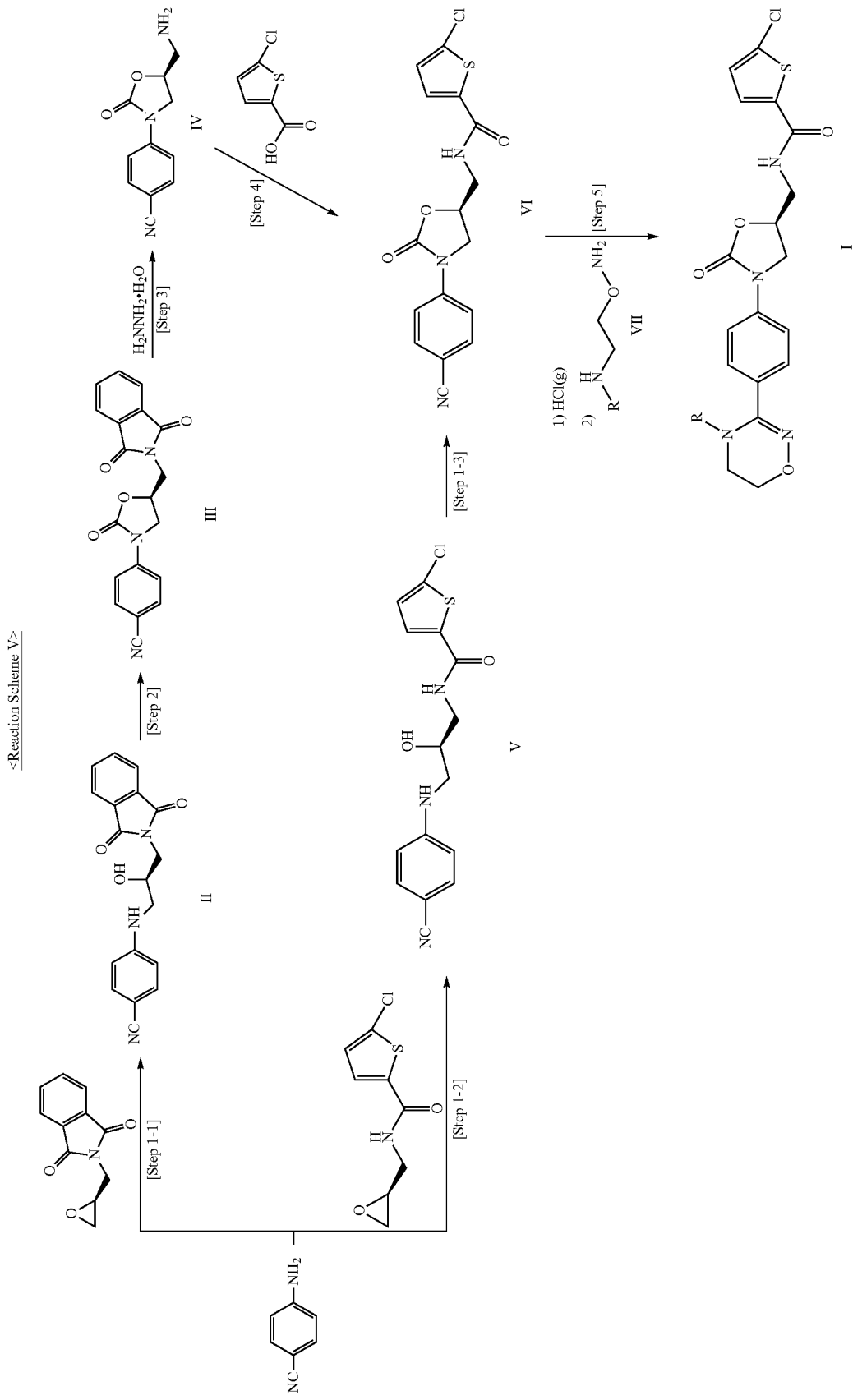
<Reaction Scheme V>

Further, the diamine compound of Formula (VII) may be prepared as shown in Reaction Scheme (VI).

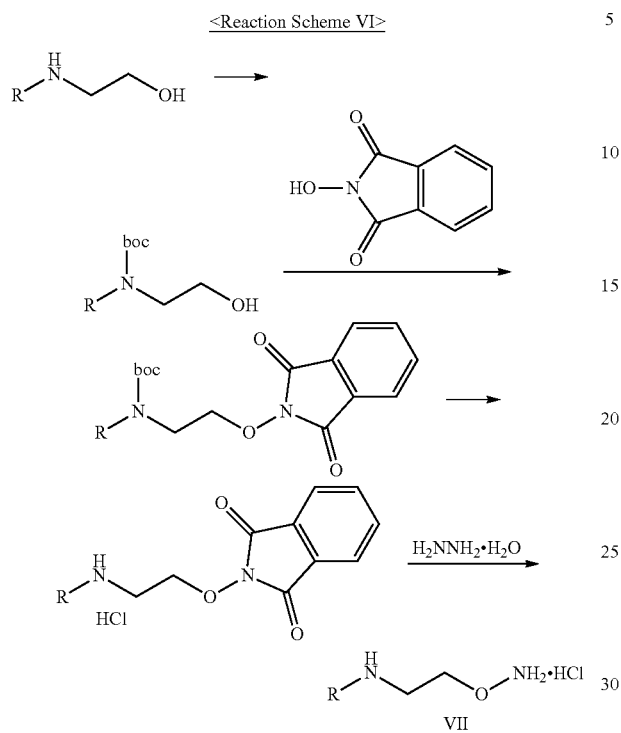

<Reaction Scheme VI>

The compound of Formula (VII) may be prepared by treating an ethanolamine as a starting material with Boc$_2$O to protect the amine group with Boc, then conducting a Mitsunobu reaction with hydroxyphthalimide in a hydrochloric acid condition to remove the Boc protective group, and treating with hydrazine to remove the phthalimide group.

The derivative of Formula (I) may be in the form of one of various salts, and the salts possibly used include all pharmaceutically acceptable salts. The pharmaceutically acceptable salts include an acid addition salt formed by a pharmaceutically acceptable free acid. The free acid includes both inorganic and organic acids, and examples of the inorganic acids include hydrochloric acid, bromic acid, sulfuric acid and phosphoric acid, and examples of the organic acids include citric acid, acetic acid, lactic acid, maleic acid, fumaric acid, gluconic acid, methanesulfonic acid, glyconic acid, succinic acid, 4-toluenesulfonic acid, trifluoroacetic acid, galacturonic acid, embonic acid, glutamic acid, and aspartamic acid. Further, the present invention includes a hydrate of the salt of the above oxazolidinone derivative, and a hydrate form having the crystallization is beneficial when the salt is hygroscopic.

The solvent and reagent used in the present invention may be substituted with a functional substitute or derivative known to one with skill in the art, and the reaction condition such as reaction time and temperature, etc., may be adjusted for optimization. The final product may be isolated from the reaction, and if necessary, it may be further purified in accordance with common methods in the art, such as extraction, crystallization, and trituration processes.

The following Examples are given for the purpose of illustration only, and are not intended to limit the scope of the invention.

Preparation Example 1

Preparation of Compound (VII-A)

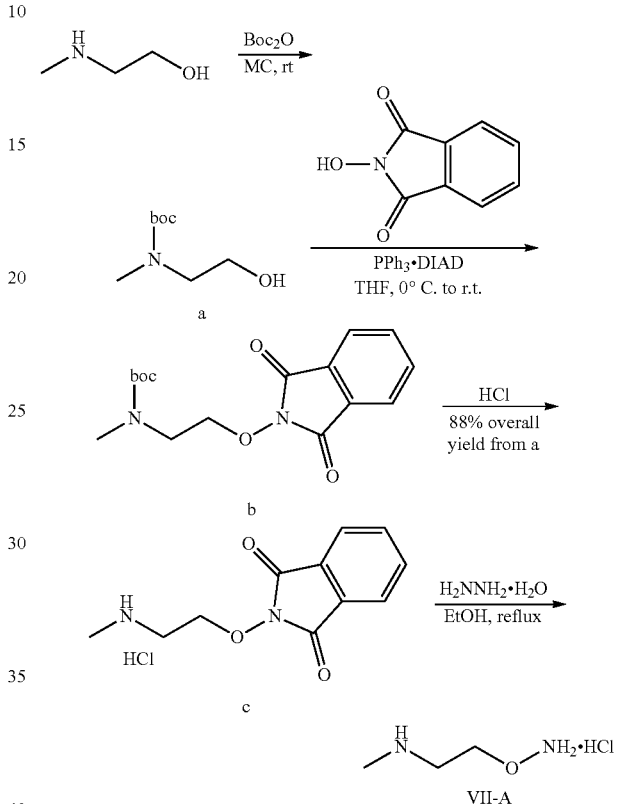

Preparation of Compound (a)

2-(methylamino)ethanol (90.1 g, 1.2 mol) was dissolved in 1.2 L of methylene chloride, and Boc$_2$O (218 g, 1 mol) was slowly added thereto while stirring at 0° C., followed by at room temperature for 3 hours. The reaction mixture was sequentially washed with 700 mL of an aqueous solution of saturated ammonium chloride, and 300 mL of water. The washed mixture was dehydrated using anhydrous sodium sulfate and concentrated under a reduced pressure, to obtain the compound (a) (175 g, 1 mol, 100%) as an oil with no color.

TLC: $R_f$=0.5 (50% EtOAc in Hex) visualized with Ce—Mo stain $^1$H NMR (600 MHz, CDCl$_3$) δ 1.47 (s, 9H), 2.88 (br s, 1H), 3.41 (br s, 2H), 3.76 (br s, 2H)

Preparation of Compound (b)

The compound (a) (90 g, 0.514 mol) was dissolved in 1.5 L of tetrahydrofuran, N-hydroxyphthalimide (88.0 g, 539 mol) and triphenylphosphine (141 g, 0.539 mol) were added thereto while stirring at 0° C. Then, diisopropyl azodicarboxylate (106 mL, 0.539 mol) was slowly added thereto and the mixture was stirred for 3 hours while increasing the temperature to room temperature. The reaction mixture was concentrated under a reduced pressure and 600 mL of isopropylether was added thereto. The resulting mixture was stirred at 0° C. for 1 hour, and the triphenylphosphineoxide formed as a white solid was removed by filtration. The solid was washed again with 200 mL of isopropylether cooled to 0° C., and mixed with a first filtrate, followed by concentration under a reduced pressure, to obtain a compound consisting of compound (b) and 10~15% of diisopropyl hydrazodicarboxylate (198 g, 120%).

TLC: $R_f$=0.4 (25% EtOAc in Hex)

$^1$H NMR (600 MHz, CDCl$_3$) δ 1.46 (d, J=16.2 Hz, 9H), 3.04 (d, J=15 Hz, 3H), 3.63 (br s, 2H), 4.34 (d, 28.2 Hz, 2H), 7.76 (br s, 2H), 7.84 (br s, 2H)

Preparation of Compound (c)

The compound (b) (198 g, 0.514 mol) was dissolved in 260 mL of 1,4-dioxane and 4M-hydrochloric acid (0.385 L, 1.54 mol) in 1,4-dioxane was slowly added thereto while stirring at 0° C. using an mechanical stirrer. The resulting mixture was stirred at room temperature for 4 hours, followed by at 0° C. for 1 hour. The white solid formed after the reaction was filtered and washed with 200 mL of 1,4-dioxane cooled to 0° C., to obtain the compound (c) having boc removed (116 g, 88%: yield of two stages from compound a) as a while solid.

$^1$H NMR (600 MHz, DMSO-d$_6$) δ 2.66 (s, 3H), 3.30 (t, J=5.4 Hz, 2H), 4.46 (t, J=5.4 Hz, 2H), 7.88-7.92 (m, 4H), 9.31 (br s, 1H)

Preparation of Compound (VII-A)

The compound (c) (53 g, 0.21 mol) was dissolved in 1.5 L of ethanol, and hydrazine monohydrate (25.1 mL, 0.518 mol) was added thereto while stirring at room temperature using mechanical stirrer, followed by for 4 hours while refluxing. The reaction mixture was cooled to 0° C. and stirred for 1 hour. The resulting solid (phthalhydrazide) was filtered and washed with 100 mL of ethanol cooled to 0° C., and the filtrate was concentrated under a reduced pressure. Then, 250 mL of methylene chloride and 500 mL of toluene were added thereto, followed by re-concentration under a reduced pressure, and 250 mL of toluene was added, followed by re-concentration under a reduce pressure. The concentration process was repeated two times to remove an excess amount of hydrazine, to obtain a compound (VII-A) (25.1 g, 96%) as a white solid.

TLC: $R_f$=0.3 (EtOAc/MeOH/AcOH=4/2/1) visualized with KMnO4 stain $^1$H NMR (600 MHz, DMSO-d$_6$) δ 2.54 (s, 3H), 3.08 (t, J=4.8 Hz, 2H), 3.74 (t, J=4.8 Hz, 2H)

Example 1

Preparation of Compound (I-A)

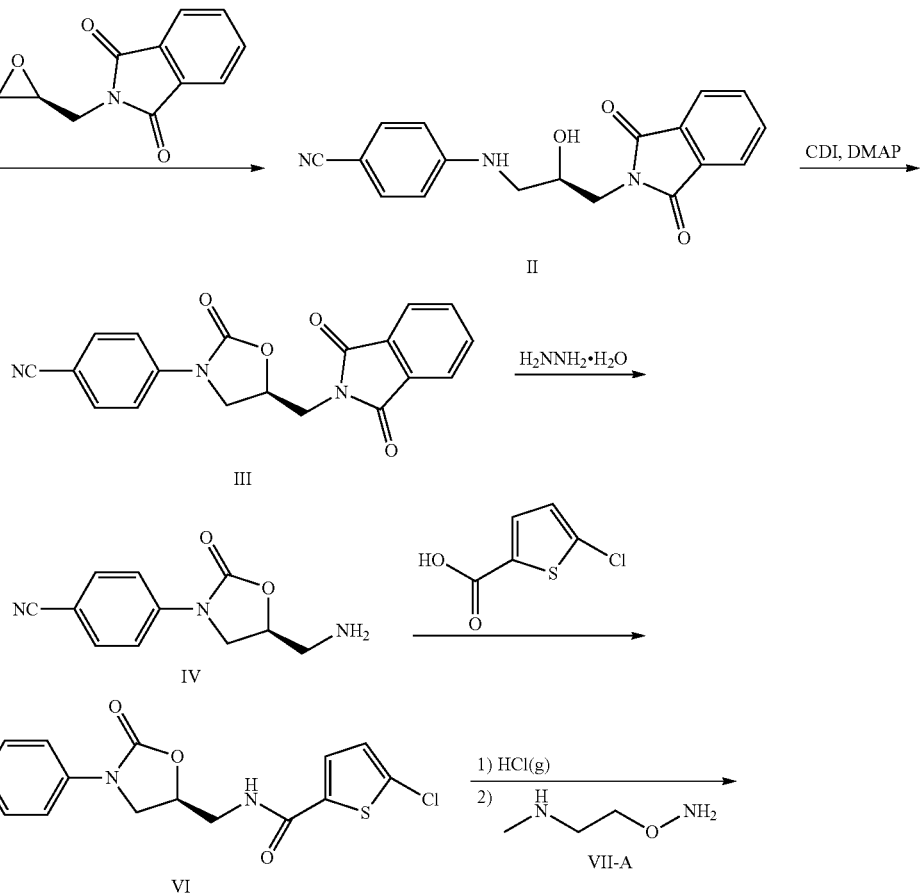

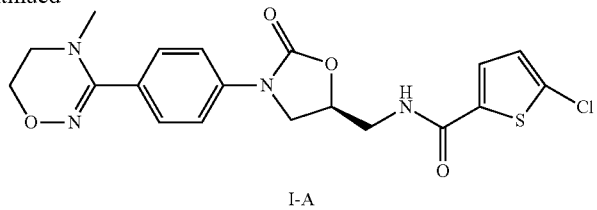

I-A

Preparation of Compound (II)

A mixture of 4-aminobenzonitrile (52.0 g, 0.440 mol) and (S)-glycidyl phthalimide (89.4 g, 0.440 mol) was stirred at 105° C. for 13 hours. The reaction mixture was cooled to 60° C., and the resulting solid with amorphous lump shape was pulverized. Then, 3.0 L of an isopropanol/methylene chloride solution (1:2) was added thereto, and stirred for 2 hours while refluxing (at the time, the solid with amorphous lump shape are dissolved and a light microcrystalline solid is formed). The suspension was distilled to remove 2 L of methylene chloride while further adding 1.0 L of isopropanol thereto. Then, the suspension was kept at room temperature for 15 hours, and stirred at 0° C. for 1 hour, and filtered under a reduced pressure. The solid thus obtained was washed with 300 mL of isopropanol cooled to 0° C. and dried to obtain the compound (II) (122 g, 84%) as a light yellow solid.

TLC: $R_f$=0.3 (50% EtOAc/Hex)

$^1$H NMR (600 MHz, DMSO-$d_6$) δ 7.90-7.82 (m, 4H), 7.45 (d, J=7 Hz, 2H), 6.70 (d, J=7 Hz, 2H), 4.07-4.14 (m, 1H), 3.64-3.58 (m, 2H), 3.22-3.18 (m, 1H), 3.13-3.17 (m, 1H)

Preparation of Compound (III)

The compound (II) (121 g, 0.367 mol) was dissolved in 1.4 L of dimethylformamide, and 1,1-carbonyldiimidazole (71.4 g, 0.440 mol) and 4-dimethylaminopyridine (9.0 g, 73 mmol) were added thereto. The resulting mixture was stirred at 80° C. for 13 hours, followed by at 90° C. for 23 hours. The reaction mixture was concentrated under a reduced pressure while maintaining the temperature to 80° C., to remove dimethyl formamide. The resulting solid was pulverized, and 800 mL of isopropanol was added thereto, and stirred for 3 hours while refluxing. The suspension was slowly cooled to room temperature, followed by at 0° C. for 1 hour, and was filtered under a reduced pressure, to obtain a light yellow solid. The solid was washed with 200 mL of isopropanol and dried to obtain the compound (III) (121 g, 95%).

TLC: $R_f$=0.8 (50% EtOAc in Hex)

$^1$H NMR (600 MHz, CDCl$_3$) δ 7.95-7.83 (m, 6H), 7.70 (d, J=9.0 Hz, 2H), 7.70 (d, J=9 Hz, 2H), 5.03-4.95 (m, 1H), 4.26 (t, J=9 Hz, 1H), 4.03 (dd, J=15, 8.4 Hz, 1H), 3.99-3.91 (m, 2H)

Preparation of Compound (VI)

The compound (III) (121 g, 0.348 mol) was dissolved in 2.2 L of a methanol/methylene chloride solution (1/1), hydrazine monohydrate (50 mL, 1.0 mol) was added thereto, and the resulting mixture was stirred for 5 hours using a mechanical stirrer while refluxing. The reaction mixture was cooled to room temperature, and resulting white solid (phthalhydrazide) was removed by filtration. The filtrate was stirred at 0° C. for 2 hours, and further precipitated phthalhydrazide was removed by filtration. The filtrate was concentrated, and resulting solid was pulverized. Then, 1 L of isopropanol was added thereto, and stirred at room temperature for 1 hour, followed by at 0° C. for 1 hour. The suspension was filtered under a reduced pressure to obtain a light yellow solid. The solid was washed three times each with 100 mL of isopropanol and 100 mL of diethylether, to obtain the compound (IV) (73.6 g, 97%).

TLC: Rf=0.2 (EtOAc/MeOH/AcOH=8/2/1)

Preparation of Compound (VI)

5-chlorothiopene-2-carboxylic acid (69.8 g, 0.429 mol) was dissolved in 1.5 L of dimethylformamide, and 4-hydroxybenzotriazole hydrate (58.1 g, 0.429 mol), N,N-diisopropylethylamine (150 mL, 0.859 mol), and the compound of Formula (IV) (71.8 g, 0.330 mol) were added thereto. The resulting mixture was cooled to 0° C., and 1-[3-(dimethylamino)propyl]-3-ethylcarbodiimide hydrochloric acid salt (95.0 g, 0.496 mol) was added thereto, and stirred at room temperature for 15 hours. Then, 1 L of cyclohexane and 3 L of distilled water were added to the reaction mixture, and stirred for 2 hours using a mechanical stirrer. The resulting ivory solid was filtered and the isolated was washed with 200 mL of distilled water and 500 mL of cyclohexane, to obtain the compound (VI) (97.5 g, 82%).

TLC: $R_f$=0.8 (EtOAc/MeOH/AcOH=8/2/1)

$^1$H NMR of an analytical sample (400 MHz, DMSO-$d_6$) δ 8.92 (t, J=5.6 Hz, 1H), 7.80 (d, J=9 Hz, 2H), 7.67 (d, J=9 Hz, 2H), 7.62 (d, J=4 Hz, 1H), 7.14 (d, J=4 Hz, 1H), 4.88-4.78 (m, 1H), 4.17 (t, J=9.2 Hz, 1H), 3.83 (dd, J=9.2, 6 Hz, 1H), 3.56 (t, J=5 Hz, 2H)

Preparation of Compound (I-A)

The compound (VI) (20.0 g, 55.3 mmol) was added to 400 mL of anhydrous methanol, and hydrochloric acid gas was bubbled therethrough at 0° C. for 2 hours, warmed to room temperature, and stirred for 3 hours (a clear suspension was formed). The solvent and residual hydrochloric acid were removed under a reduced pressure, acetic acid (750 mL) and the compound (VII-A) synthesized in Preparation Example 1 (10.5 g, 82.9 mmol) were added thereto, and the resulting mixture was stirred for 16 hours while refluxing. The reaction mixture was concentrated under a reduced pressure, and dissolved in 750 mL of 1N HCl. The aqueous solution was extracted three times each with 300 mL of ethyl acetate to remove impurities in the organic layer. The aqueous layer was neutralized with 2N Na$_2$CO$_3$. The solid formed was isolated and was dissolved in 400 mL of methanol/chloroform solution (1/19). The resulting solution was treated with a silica-celite pad (column diameter=12 cm, the lower part: silica of 3 cm by height (used amount of silica=55 g), upper part: celite of 1.5 cm by height, a filter paper is placed on the upper side), and then with 600 mL of a methanol/chloroform solution (1/19). The eluted solution was distilled under a reduced pressure, to obtain the title compound as a white solid (13.2 g, 55%).

TLC: $R_f$=0.4 (5% MeOH in MC)

$^1$H NMR (400 MHz, CDCl$_3$) δ 7.54 (d, J=9.0 Hz, 2H), 7.44 (d, J=9.0 Hz, 2H), 7.34 (d, J=4.2 Hz, 1H), 6.89 (br t, 1H), 4.80 (m, 1H), 4.12 (t, J=4.8 Hz, 2H), 4.04 (t, J=9.0 Hz, 1H), 3.85-3.80 (m, 2H), 3.69-3.64 (m, 1H), 3.45 (t, J=4.8 Hz, 2H), 2.76 (s, 3H)

LCMS: 435 (M+H+) for C$_{19}$H$_{19}$ClN$_4$O$_4$S

While the invention has been described with respect to the above specific embodiments, it should be recognized that various modifications and changes may be made to the invention by those skilled in the art which also fall within the scope of the invention as defined by the appended claims.

What is claimed is:

1. A method for preparing an oxazolidinone derivative having a cyclic amidrazone group of Formula (I) or a pharmaceutically acceptable salt thereof, comprising treating the cyano group of the oxazolidinone compound of Formula (VI) with hydrochloric acid, and conducting a cyclization reaction of the resulting product with the diamine compound of Formula (VII):

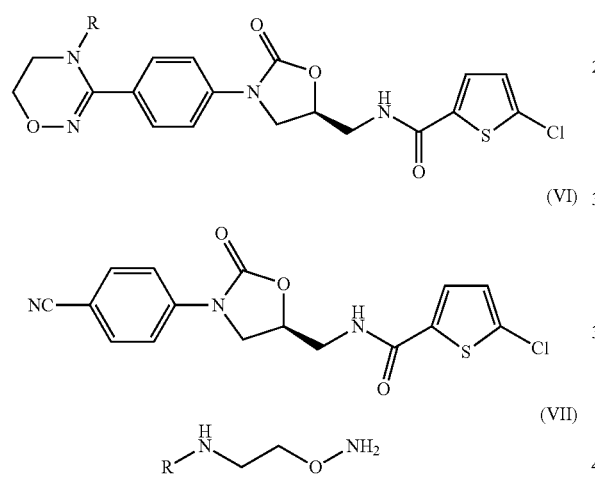

wherein,
R is hydrogen, C$_1$-C$_7$ alkyl, C$_3$-C$_7$ cycloalkyl, or C$_6$-C$_{12}$ aryl.

2. The method of claim 1, wherein the oxazolidinone compound of Formula (VI) is prepared by:
   1) conducting a condensation reaction of 4-aminobenzonitrile with (S)-glycidyl phthalimide, to obtain the compound of Formula (II);
   2) carbonylating the compound of Formula (II) with ethyl chloroformate or 1,1'-carbonyldiimidazole to obtain the oxazolidinone ring compound of Formula (III);
   3) treating the oxazolidinone compound of Formula (III) with hydrazine so as to remove the phthalimide nitrogen atom protective group, to obtain the primary amine compound of Formula (IV); and
   4) treating the primary amine compound of Formula (IV) with 5-chlorothiopene-2-carboxylic acid to obtain the compound of Formula (VI) having introduced 5-chlorothiopene-2-carbonyl group

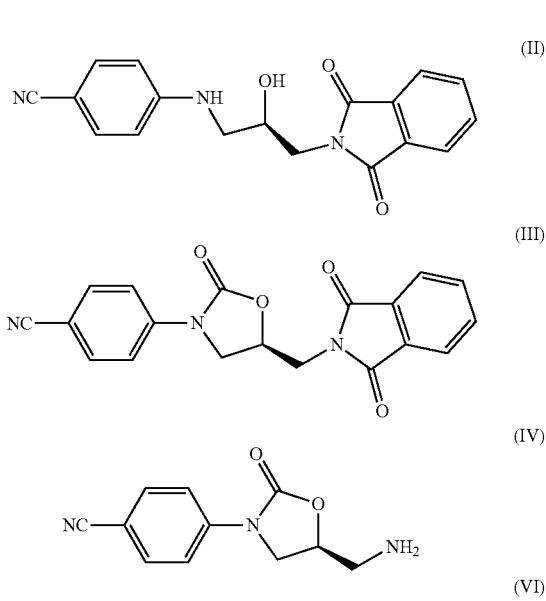

3. The method of claim 1, wherein the oxazolidinone compound of Formula (VI) is prepared by:
   1-2) treating 4-aminobenzonitrile with 5-chloro-N-((S)-oxiran-2-yl)methyl)thiopene-2-carboxamide to obtain the compound of Formula (V); and
   1-3) carbonylating the compound of Formula (V) with ethyl chloroformate or 1,1'-carbonyldiimidazole to obtain the oxazolidinone ring compound of Formula (VI)

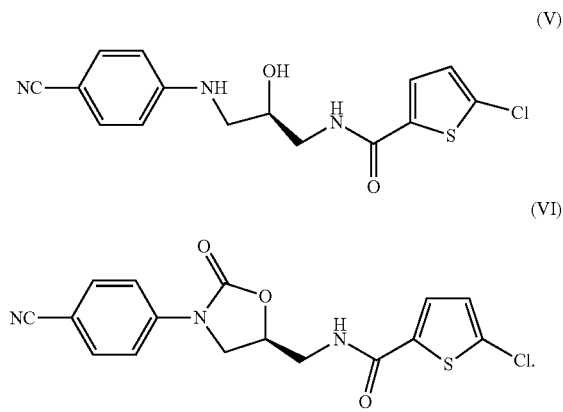

* * * * *